(12) United States Patent
Wolff et al.

(10) Patent No.: US 8,591,803 B2
(45) Date of Patent: Nov. 26, 2013

(54) PROCESS FOR PRODUCING COMPONENTS CONSISTING OF MAGNESIUM OR MAGNESIUM ALLOY BY SINTERING

(75) Inventors: Martin Wolff, Geesthacht (DE); Thomas Ebel, Handorf (DE); Norbert Hort, Lüneburg (DE)

(73) Assignee: Helmholtz-Zentrum Geesthacht Zentrum für Material- und Küstenforschung GmbH, Geesthacht (DE)

( * ) Notice: Subject to any disclaimer, the term of this patent is extended or adjusted under 35 U.S.C. 154(b) by 543 days.

(21) Appl. No.: 12/766,113

(22) Filed: Apr. 23, 2010

(65) Prior Publication Data
US 2010/0274292 A1 Oct. 28, 2010

(30) Foreign Application Priority Data
Apr. 27, 2009 (DE) .......................... 10 2009 019 041

(51) Int. Cl.
*B22F 1/00* (2006.01)
(52) U.S. Cl.
USPC .................................. 419/38; 419/56; 75/249

(58) Field of Classification Search
USPC .............................................................. 419/38
See application file for complete search history.

(56) References Cited

U.S. PATENT DOCUMENTS

| 2,221,263 | A |   | 11/1940 | Nelson et al. |   |
|---|---|---|---|---|---|
| 3,359,095 | A |   | 12/1967 | Foerster et al. |   |
| 5,225,155 | A | * | 7/1993 | Hampton et al. | ............... 419/56 |
| 2009/0081313 | A1 |   | 3/2009 | Aghion et al. |   |

FOREIGN PATENT DOCUMENTS

| EP | 524438 A2 | 1/1993 |
|---|---|---|
| EP | 1959025 A1 | 8/2008 |

* cited by examiner

*Primary Examiner* — Roy King
*Assistant Examiner* — Christopher Kessler
(74) *Attorney, Agent, or Firm* — Marshall, Gerstein & Borun LLP

(57) ABSTRACT

The present invention relates to a process for producing components consisting of magnesium or magnesium alloy by sintering. This process makes it possible, for the first time, to produce components consisting of magnesium or magnesium alloy which provide outstanding elasticity together with a sufficient strength. Materials of this type can be used as biocompatible endosseous implant materials.

20 Claims, 3 Drawing Sheets

PROCESS FOR PRODUCING COMPONENTS CONSISTING OF MAGNESIUM OR MAGNESIUM ALLOY BY SINTERING

CROSS-REFERENCE TO RELATED APPLICATION

The present application claims the benefit of priority of German Patent Application No. 10 2009 019 041.4 filed Apr. 27, 2009. The entire text of the priority application is incorporated herein by reference in its entirety.

FIELD OF THE INVENTION

The present invention relates to a process for producing components consisting of magnesium or magnesium alloy by sintering. To date, it has not been possible to produce components consisting of magnesium or a magnesium alloy by sintering with a usable strength, in particular a usable compressive strength, and a usable modulus of elasticity.

BACKGROUND AND PRIOR ART

Components of this type would be desirable, for example, as biocompatible and/or biodegradable implant materials. The disadvantage of existing biocompatible implant materials, such as steel or titanium alloys, is that they have a considerably higher modulus of elasticity and density value than bone material. Therefore, the implant may become loose. A further problem of these implant materials is that the metallic implant does not biodegrade by itself in the body, and the implant has to be removed by an operation.

In order to improve removability, known metallic implants also have smooth surfaces. However, these are disadvantageous if bone tissue is to grow into the implant in order to provide improved stabilization of the transition region.

Owing to their low strength compared with metallic implant materials, bioresorbable and/or biodegradable, polymeric implant materials, such as those made from polylactides, can only be used in fields of application where the material is subjected to a small amount of loading.

Therefore, it is an object of the present invention to provide a component which is suitable as biocompatible implant material, has a modulus of elasticity which is adapted to the bone material along with sufficient strength, and to which a porous surface can be imparted, and also a process for producing said component. At the same time, the implant materials should also be bioresorbable and/or biodegradable.

A further object of the invention is to produce a component consisting of magnesium or a magnesium alloy by sintering, this component having a usable strength, such as compressive strength, and a usable modulus of elasticity, so that this component is suitable as biocompatible implant material, for example in the form of screws, pins, bolts, hooks and/or plates.

The object is achieved by a process for producing components consisting of magnesium or magnesium alloys by sintering, in which process a green compact consisting of magnesium powder and/or a magnesium alloy powder and, if appropriate, an additional alloying constituent is first of all produced, the green compact is transferred into an inner sintering crucible, the inner sintering crucible is placed into an outer sintering crucible, the inner sintering crucible which has been placed in the outer sintering crucible is surrounded with a getter material which is able to bond gases and/or impurities, the outer sintering crucible with the inner sintering crucible inserted into it and the getter material is heated to sintering temperature, and the outer sintering crucible with the inner sintering crucible inserted into it and the getter material is allowed to cool after the green compact has been sintered in order to produce the component consisting of magnesium or magnesium alloy.

This object is also achieved by a component which consists of magnesium or magnesium alloy and can be produced by the above process, and also by the use of the component for producing endosseous implant materials which are preferably in the form of a screw, a pin, a bolt, a hook or a plate. The dependent claims specify preferred embodiments.

The starting materials, such as magnesium powder, magnesium alloy powder and/or a powder mixture, are preferably pressed with a pressure of 50 to 125 MPa, and more preferably 75 to 100 MPa.

A decisive factor for successful sintering of the magnesium or of the magnesium alloy or else of a magnesium powder mixture is the use of a getter material. Within the context of the present invention, a getter material is a material which is able to bond gases and/or impurities during the sintering process. The preferred getter material is magnesium, in particular magnesium powder.

The getter material preferably surrounds the inner sintering crucible which has been placed in the outer sintering crucible. With particular preference, the inner sintering crucible which has been placed in the outer sintering crucible is completely enveloped by the getter material. Alternatively, it is possible to select a so-called "labyrinth sintering crucible arrangement", in which case potential impurities such as oxygen first have to pass completely through the bed of getter material before they reach the inner crucible region. In the case of a "labyrinth sintering crucible arrangement", it is possible for a plurality of inner sintering crucibles to be arranged one above another, separated by intermediate bases, and these crucibles are preferably covered by a supporting sleeve and held by a retort.

The inner and/or the outer sintering crucible can be made from any material which can withstand sintering temperatures. With particular preference, the inner and/or the outer sintering crucible are produced from steel, preferably unalloyed steel.

The component consists of magnesium or a magnesium alloy. The magnesium alloy is preferably a magnesium-calcium alloy, preferably with a calcium content of up to 1.5% by mass, more preferably 0.2 to 1.0% by mass, most preferably 0.6 to 0.8% by mass. A component which consists of such a magnesium-calcium alloy may be produced, for example, by using magnesium in combination with calcium hydride or magnesium in combination with a magnesium-calcium master alloy as charge materials in an appropriate amount. Examples for the production of a magnesium-calcium alloy (MgCa1) using a calcium hydride or a magnesium-calcium master alloy are as follows:

(a) Mg (98.9%)+CaH$_2$ (1.1%)→MgCa1 (hy)
(b) Mg (98.8%)+MgCa82 (1.2%)→MgCa1 (eu)
(c) Mg (85.5%)+MgCa7 (14.5%) MgCa1 (al)

By reducing the amount of calcium hydride or magnesium-calcium master alloy, magnesium-calcium alloys having a calcium content of less than 1% by mass are obtained.

Components which consist of a magnesium-calcium alloy having a calcium content of up to 1.5% by mass, preferably up to 1% by mass, most preferably up to 0.8% by mass, are preferred to components which consist of pure magnesium. Comparative tests have shown that these alloys have an elasticity and strength which are much improved compared with pure magnesium.

The master alloys which can advantageously be used for producing the components, according to the invention, consisting of magnesium-calcium alloy are the eutectic magnesium-calcium alloys MgCa16 or MgCa82 or a magnesium-calcium alloy having a calcium content of less than 16.2% by mass.

Furthermore, it is also possible to produce other magnesium alloys, such as WE43 (4% yttrium, 3% rare earth elements, remainder magnesium) or W4 (4% yttrium, remainder magnesium), by sintering, as per the process according to the invention. With preference, these alloys according to the invention are also used in medical engineering.

The sintering preferably takes place in a shielding-gas atmosphere or in vacuo. The preferred shielding gas is argon. The sintering preferably takes place at temperatures below the melting temperature of magnesium. The preferred sintering temperature is 600° C. to 642° C. The heating rate from ambient temperature to the sintering temperature is preferably 0.1 to 20 K/min, more preferably 1 to 10 K/min, most preferably 3 to 6 K/min. The sintering preferably lasts for 4 to 64 hours. A further extension to the sintering time can further improve the strength properties of the specimens. The subsequent cooling should preferably take place as quickly as possible, but it is also possible to merely switch off the furnace. However, it is advantageous that the getter material is held under shielding gas or in vacuo for so long that it can no longer ignite.

BRIEF DESCRIPTION OF THE DRAWINGS

The invention is explained by the examples which follow, in which.

DETAILED DESCRIPTION

Example 1

Figure 1:
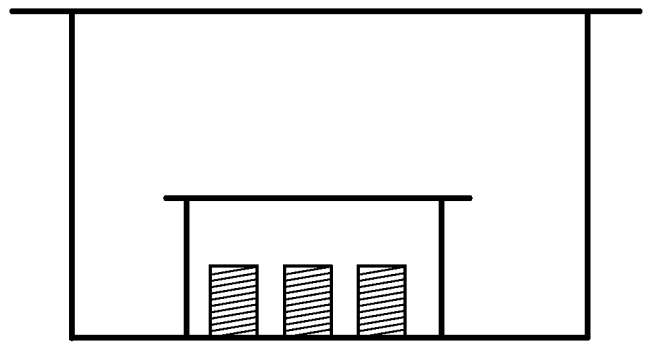
FIG. 1: is a cross-sectional view of an outer sintering crucible having an inner sintering crucible (No. 3) placed therein and three green compacts introduced into the sintering crucibles, no getter material being present.
Figure 2:
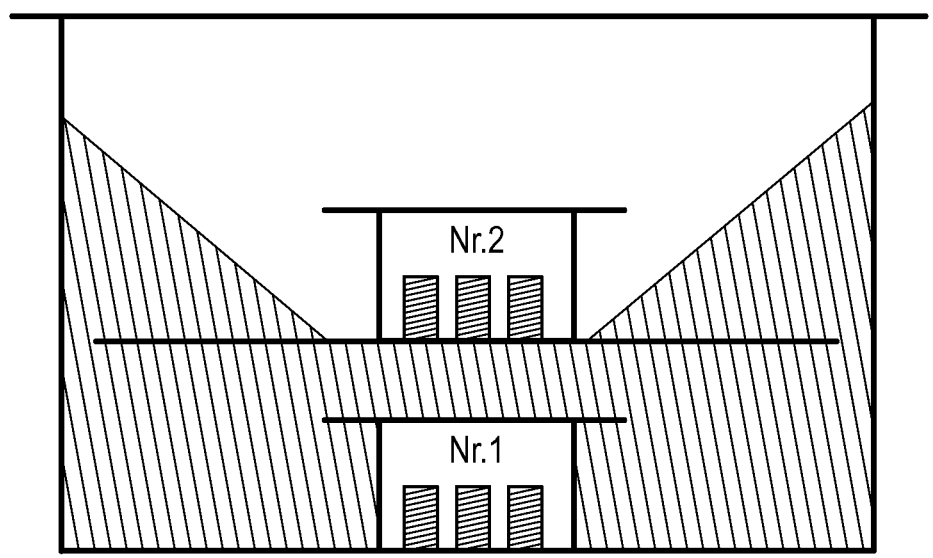
FIG. 2: is a cross-sectional view of an outer sintering crucible having two inner sintering crucibles placed therein and three green compacts introduced into each of the inner sintering crucibles, where one inner sintering crucible (No. 1) is completely enveloped by getter material and a further inner sintering crucible (No. 2) is partially surrounded by getter material.

A total of twelve green compacts consisting of magnesium powder were pressed. Five magnesium green compacts were placed in an inner sintering crucible (sintering crucible No. 1), a further four magnesium green compacts were placed in an inner sintering crucible (sintering crucible No. 2), and finally a further three magnesium green compacts were placed in an inner sintering crucible (sintering crucible No. 3). Sintering crucible No. 3 was placed in an outer sintering crucible, and not surrounded with getter material (see FIG. 1). Sintering crucible No. 1 was likewise placed in an outer sintering crucible and completely enveloped by magnesium powder as getter material, sintering crucible No. 2 was placed above sintering crucible No. 1 and magnesium powder was added as getter material until sintering crucible No. 2 was only surrounded—not completely enveloped—by sintering material (see FIG. 2). All of the green compacts were sintered in a sintering furnace in an argon atmosphere for 64 hours at 630° C.

Figure 3:
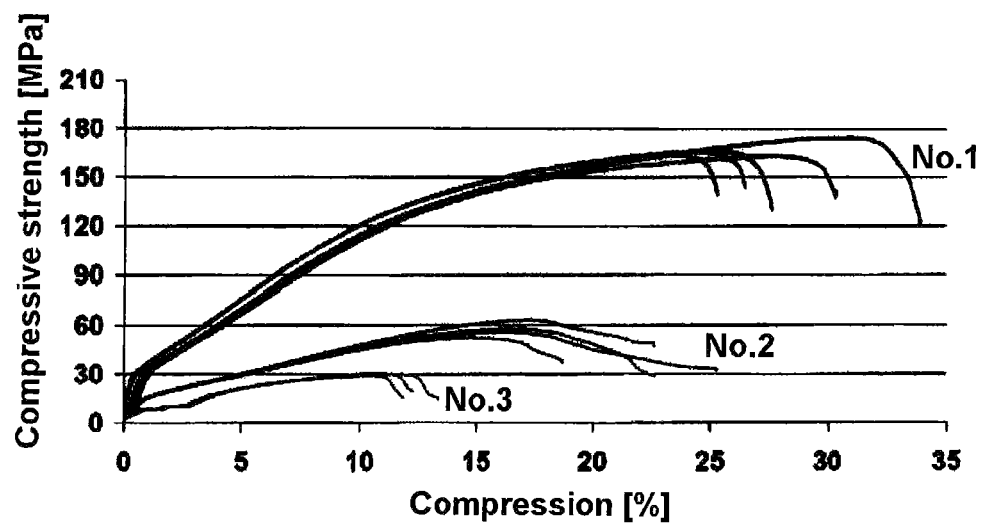
FIG. 3: shows the compression [%] as a function of the compressive strength [MPa] of the three specimens No. 1, No. 2 and No. 3.

FIG. 3 shows the compression [%] as a function of the compressive strength [MPa] of the three specimens No. 1, No. 2 and No. 3. It can be seen in FIG. 3 that specimen No. 3 (sintered without getter material) has a very low compression at failure. The material also has low elasticity. On the other hand, the specimens sintered using a getter material show a very high compression at failure and outstanding elasticity values, specimen No. 1 (sintered with complete enveloping by getter material) having the best values.

|  | Compressive strength [MPa] | 0.2% Elongation limit [MPa] | Modulus of elasticity [GPa] | Compression at failure [%] | Residual porosity [%] |
|---|---|---|---|---|---|
| Specimen No. 1 | 167 ± 4.5 | 35 ± 4 | 8 ± 3 | 26 ± 4 | 14 ± 1 |
| Specimen No. 2 | 57 ± 4.6 | 18 ± 1 | 2.5 ± 0.5 | 20 ± 3 | 22 ± 1 |
| Specimen No. 3 | 30 ± 1 | 13.5 ± 6 | 1.2 ± 0.3 | 11 ± 1 | 24 ± 0.3 |

Example 2

Green compacts consisting of magnesium powder and mixtures of magnesium with calcium hydride or of magnesium-calcium alloys were pressed in the following ratios with 100 MPa:

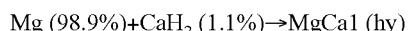
Mg (98.9%)+CaH$_2$ (1.1%)→MgCa1 (hy)

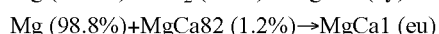
Mg (98.8%)+MgCa82 (1.2%)→MgCa1 (eu)

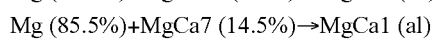
Mg (85.5%)+MgCa7 (14.5%)→MgCa1 (al)

Finally, green compacts consisting of magnesium powder and a magnesium-calcium alloy were pressed in the following ratios:

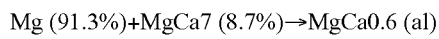
Mg (91.3%)+MgCa7 (8.7%)→MgCa0.6 (al)

The magnesium green compacts or magnesium alloy green compacts were placed in an inner sintering crucible. The inner sintering crucible was placed in an outer sintering crucible, and surrounded completely with getter material. All of the green compacts were sintered in a sintering furnace in an argon atmosphere for 64 hours at 630° C.

|  | Compressive strength [MPa] | 0.2% Elongation limit [MPa] | Modulus of elasticity [GPa] | Compression at failure [%] | Residual porosity [%] |
| --- | --- | --- | --- | --- | --- |
| pure Mg | 184 ± 7 | 36.2 ± 2.6 | 6.2 ± 2.1 | 26.7 ± 2.7 | 13.6 ± 0.4 |
| MgCa1 (hy) | 217 | 58.4 | 8.8 | 20.6 | 8.0 ± 0.3 |
| MgCa1 (eu) | 236 ± 18.6 | 59.6 | 4.1 | 23.4 | 9.7 ± 0.2 |
| MgCa1 (al) | 255 | 69.4 | 5.9 | 25.5 | 2.1 ± 0.2 |
| MgCa0.6 (al) | 283.7 ± 1.5 | 65.6 ± 4.4 | 8.6 ± 1.6 | 29.6 ± 0.5 | 1.4 ± 0.2 |
| MgCa0.6 (cast) | 273.2 ± 6.1 | 114.4 ± 15.1 | 44.5 ± 0.8 | — | — |

Figure 4:
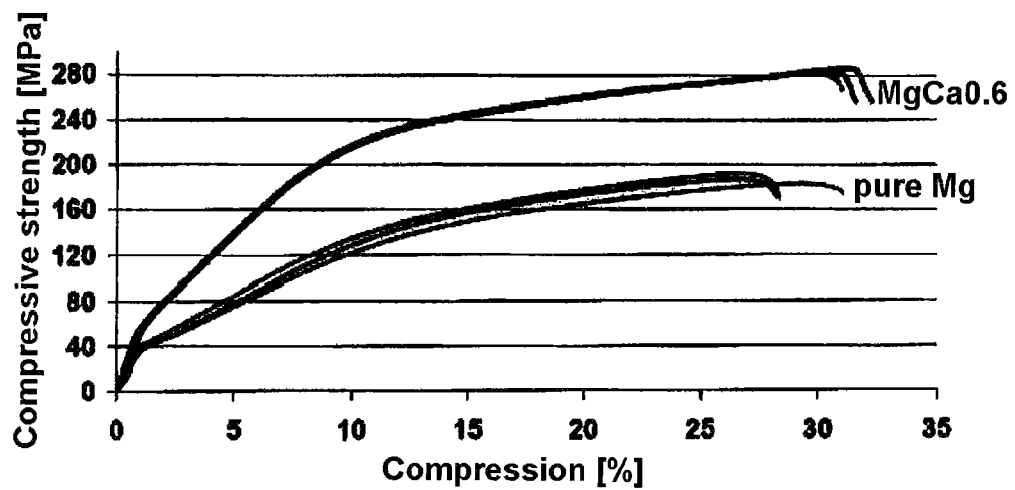
FIG. 4: shows the compression [%] as a function of the compressive strength [MPa] of pure magnesium (produced by the process according to the invention) and of an MgCa0.6 alloy (likewise produced by the process according to the invention)
Figure 5:
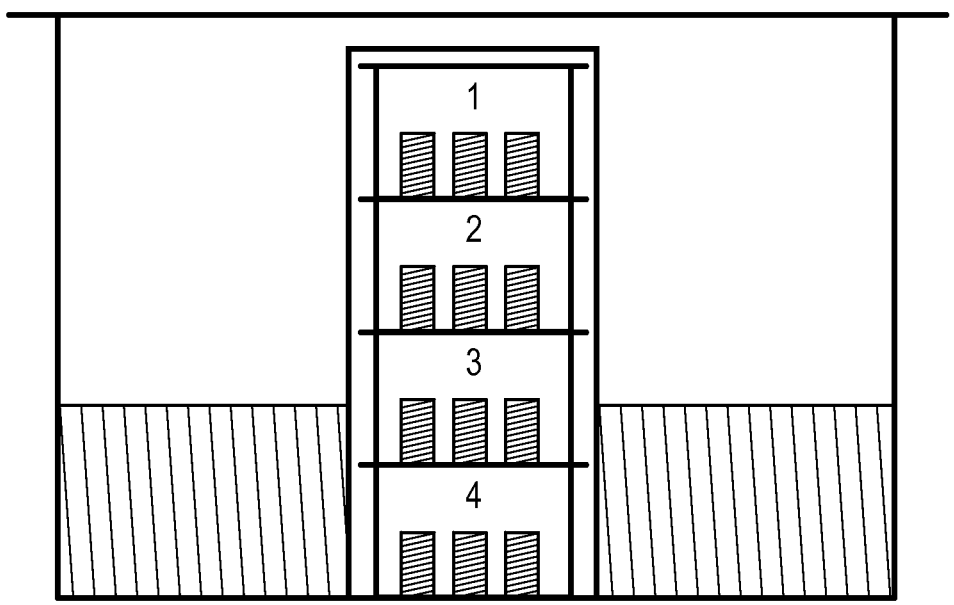
FIG. 5: is a cross-sectional view of a "labyrinth sintering crucible arrangement", where a plurality of sintering crucibles are arranged one above another, are held by a supporting sleeve and are surrounded by a retort. Here, the arrangement is selected such that any impurities in the outer crucible region first have to pass through the getter material before they can reach the inner crucible region.

FIG. 4 shows the compression [%] as a function of the compressive strength [MPa] of pure magnesium and of the MgCa0.6 alloy, each of which were produced as per Example 2.

The invention claimed is:

1. A process for producing components consisting of magnesium by sintering, comprising:
    first, producing a green compact consisting of magnesium powder,
    transferring the green compact into an inner sintering crucible,
    placing the inner sintering crucible into an outer sintering crucible,
    surrounding the inner sintering crucible, which has been placed in the outer sintering crucible, with a getter material comprising magnesium powder which is able to bond gases and/or impurities,
    heating the outer sintering crucible, with the inner sintering crucible inserted into it, and the getter material to sintering temperature of the green compact, and
    allowing the outer sintering crucible, with the inner sintering crucible inserted into it, and the getter material to cool after the green compact has been sintered in order to produce the component consisting of magnesium.

2. A process according to claim 1, wherein the green compact is produced in a shielding-gas atmosphere.

3. A process according to claim 2, wherein the shielding gas is argon.

4. A process according to claim 1, wherein the getter material consists of magnesium powder.

5. A process according to claim 1, wherein the getter material completely envelops the inner sintering crucible.

6. A process according to claim 1, wherein the outer sintering crucible, with the inner sintering crucible inserted into it, and the getter material is heated to a sintering temperature of 600° C. to 642° C.

7. A process according to claim 1, wherein the outer sintering crucible, with the inner sintering crucible inserted into it, and the getter material is heated to sintering temperature for a time period between 4 to 64 hours.

8. A process according to claim 1, wherein the outer sintering crucible, with the inner sintering crucible inserted into it, and the getter material is heated up to sintering temperature with a heating rate of 0.1 to 20 K/min.

9. A process for producing components consisting of a magnesium alloy by sintering, comprising:
    first, producing a green compact consisting of magnesium alloy powder or of magnesium powder and an additional alloying constituent,
    transferring the green compact into an inner sintering crucible,
    placing the inner sintering crucible into an outer sintering crucible,
    surrounding the inner sintering crucible, which has been placed in the outer sintering crucible, with a getter material comprising magnesium powder which is able to bond gases and/or impurities,
    heating the outer sintering crucible, with the inner sintering crucible inserted into it, and the getter material to sintering temperature of the green compact, and
    allowing the outer sintering crucible, with the inner sintering crucible inserted into it, and the getter material to cool after the green compact has been sintered in order to produce the component consisting of a magnesium alloy.

10. A process according to claim 9, wherein the additional alloying constituent comprises a magnesium-calcium master alloy that contains 2 to 17% by mass of calcium.

11. A process according to claim 9, wherein the additional alloying constituent comprises a magnesium-calcium master alloy that contains about 70 to 90% by mass of calcium.

12. A process according to claim 9, wherein the component is produced from the magnesium alloy powder that contains 0.1 to 1% of calcium.

13. Process according to claim 9, wherein the additional alloying constituent is selected from the group consisting of calcium hydride, a magnesium-calcium master alloy, and mixtures thereof.

14. A process according to claim 9, wherein the green compact is produced in a shielding-gas atmosphere.

15. A process according to claim 14, wherein the shielding gas is argon.

16. A process according to claim 9, wherein the getter material consists of magnesium powder.

17. A process according to claim 9, wherein the getter material completely envelops the inner sintering crucible.

18. A process according to claim 9, wherein the outer sintering crucible, with the inner sintering crucible inserted into it, and the getter material is heated to a sintering temperature of 600° C. to 642° C.

19. A process according to claim 9, wherein the outer sintering crucible, with the inner sintering crucible inserted into it, and the getter material is heated to sintering temperature for a time period between 4 to 64 hours.

20. A process according to claim 9, wherein the outer sintering crucible, with the inner sintering crucible inserted into it, and the getter material is heated up to sintering temperature with a heating rate of 0.1 to 20 K/min.

* * * * *